(12) United States Patent
Furrer et al.

(10) Patent No.: US 8,377,422 B2
(45) Date of Patent: Feb. 19, 2013

(54) CARBOXAMIDE DERIVATIVES HAVING COOLING PROPERTIES

(75) Inventors: Stefan Michael Furrer, Cincinnati, OH (US); Thomas Scott McCluskey, Amelia, OH (US)

(73) Assignee: Givaudan S.A., Vernier (CH)

( * ) Notice: Subject to any disclaimer, the term of this patent is extended or adjusted under 35 U.S.C. 154(b) by 89 days.

(21) Appl. No.: 12/745,019

(22) PCT Filed: Dec. 4, 2008

(86) PCT No.: PCT/CH2008/000516
§ 371 (c)(1), (2), (4) Date: Jul. 9, 2010

(87) PCT Pub. No.: WO2009/070910
PCT Pub. Date: Jun. 11, 2009

(65) Prior Publication Data
US 2011/0182833 A1 Jul. 28, 2011

Related U.S. Application Data

(60) Provisional application No. 61/005,711, filed on Dec. 7, 2007.

(51) Int. Cl.
| | |
|---|---|
| A61K 8/42 | (2006.01) |
| A61K 8/49 | (2006.01) |
| C07C 233/33 | (2006.01) |
| C07D 319/16 | (2006.01) |
| C07D 213/64 | (2006.01) |
| A61Q 11/00 | (2006.01) |
| A61Q 90/00 | (2009.01) |
| A61Q 19/00 | (2006.01) |

(52) U.S. Cl. .......... 424/49; 564/192; 549/366; 546/290; 514/625; 514/452; 514/345

(58) Field of Classification Search .................. None
See application file for complete search history.

(56) References Cited

U.S. PATENT DOCUMENTS

| | | | |
|---|---|---|---|
| 4,136,163 | A | 1/1979 | Watson et al. |
| 4,150,052 | A | 4/1979 | Watson et al. |
| 4,190,643 | A | 2/1980 | Rowsell et al. |
| 4,248,859 | A | 2/1981 | Rowsell et al. |
| 4,318,900 | A | 3/1982 | Rowsell et al. |
| 4,859,706 | A | 8/1989 | Buerstinghaus et al. |
| 7,414,152 | B2 | 8/2008 | Galopin et al. |
| 2005/0159394 | A1 * | 7/2005 | Wei ................. 514/159 |
| 2005/0187211 | A1 | 8/2005 | Wei |
| 2007/0155755 | A1 | 7/2007 | Wei |
| 2008/0096969 | A1 | 4/2008 | Ley |
| 2008/0112899 | A1 | 5/2008 | Galopin et al. |
| 2008/0227857 | A1 * | 9/2008 | Wei ................. 514/473 |
| 2010/0035938 | A1 | 2/2010 | Bell et al. |

FOREIGN PATENT DOCUMENTS

| | | |
|---|---|---|
| EP | 0 618 195 A1 | 10/1994 |
| EP | 1 000 619 A2 | 5/2000 |
| EP | 1 913 976 A1 | 4/2008 |
| FR | 2127013 | 10/1972 |
| GB | 1351761 | 5/1974 |
| GB | 1421744 A | 1/1976 |
| GB | 1457671 A | 12/1976 |
| WO | WO 2005/002582 A2 | 1/2005 |
| WO | WO 2005/020897 A2 | 3/2005 |
| WO | WO 2005/049553 A1 | 6/2005 |
| WO | WO 2005/058830 A1 | 6/2005 |
| WO | WO 2006/125334 A1 | 11/2006 |
| WO | WO 2007/019719 A1 | 2/2007 |

OTHER PUBLICATIONS

Unangst et al. in Journal of Medicinal Chemistry, 1997, 40, 4026-4029.*
Hernandez, Dolores, et al., "Potent Hypolipidemic Activity of Mimetic Amides of Fibrates Based on the 2-Methoxy-4-(2-propenyl)phenoxyacetic Scaffold", Drug Development Research, 2004, vol. 61, pp. 19-36.
Watson, H.R., et al., "New Compounds With the Menthol Cooling Effect", Journal of the Society of Cosmetic Chemists, vol. 29, No. 4, Jan. 1, 1978, pp. 185-200. XP009045124.
PCT/CH2008/00516—Written Opinion of the International Searching Authority, Jun. 29, 2009.
PCT/CH2008/00516—International Search Report, Jun. 29, 2009.
GB 0720506.5—Great Britain Search Report, Oct. 27, 2008.

* cited by examiner

*Primary Examiner* — Dennis Heyer
(74) *Attorney, Agent, or Firm* — Curatolo Sidoti Co., LPA; Joseph G. Curatolo; Salvatore A. Sidoti

(57) ABSTRACT

Compounds of formula (I)

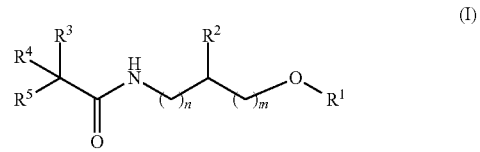

wherein $R^1$-R5, n and m have the same meaning as given in the description, having cooling properties are disclosed. Furthermore a process of their production and consumer products comprising them are disclosed.

16 Claims, No Drawings

CARBOXAMIDE DERIVATIVES HAVING COOLING PROPERTIES

CROSS REFERENCE TO RELATED APPLICATIONS

This application is a national stage application of. International Application No. PCT/CH2008/000516, filed 4 Dec. 2008, which claims priority from U.S. Provisional Patent Application Ser. No. 61/005,711, filed 7 Dec. 2007, from which applications priority is claimed, and which are incorporated herein by reference.

Provided is a new class of compounds having cooling properties. Also provided are a process of their production and consumer products comprising them.

In the flavour and fragrance industry there is an ongoing demand for compounds having unique cooling properties that provide the user with a pleasing cooling effect and which are suitable for use in a variety of products, particularly in ingestible and topically-applied products.

The most well-known cooling compound is l-menthol, which is found naturally in oil of mint. Since menthol has a strong minty odor and a bitter taste, and provides a burning sensation when used in high concentrations, a variety of other menthyl ester-based and menthyl carboxamide-based cooling compounds have been developed. One that has enjoyed substantial success is N-ethyl p-menthane-carboxamide (WS-3) and is thus also often used as a benchmark.

Another class of menthyl carboxamide-based cooling compounds, namely alkyloxy amides of p-menthane, such as N-(3-isopropoxypropyl)-2-isopropyl-5-methylcyclohexanecarboxamide, is described in Japanese Patent No. 2004059474. In addition to other compounds, 2-isopropyl-N-(2-methoxyethyl)-5-methylcyclohexane-carboxamide is described by Watson et al. (Journal of the Society of Cosmetic Chemistry (1978), 29(4), 185-200). Watson describes several classes of compounds having the menthol cooling effect but not the disadvantages associated with its volatility.

We have now found a novel class of compounds, which is capable of imparting and/or enhancing a physiological cooling effect in a product in which it is incorporated, much more effectively than the heretofore known N-alkyloxy-p-menthane-3-carboxamides.

Thus there is provided in a first aspect a compound of formula (I)

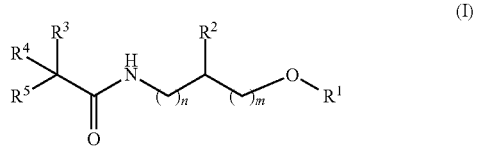

(I)

wherein
$R^1$ is selected from phenyl, phenyl substituted with 1, 2, 3 or more substitutents selected from $C_1$-$C_3$ alkyl, $C_2$-$C_4$ alkenyl, and RO wherein R is selected from hydrogen and $C_1$-$C_3$ alkyl (e.g. 2-methoxy phenyl, 4-methyl phenyl),
pyridyl (e.g. pyrid-2-yl, pyrid-3-yl), pyridyl substituted with 1, 2; 3 or more substitutents selected from $C_1$-$C_3$ alkyl; $C_2$-$C_4$ alkenyl, and RO wherein R is selected from hydrogen and $C_1$-$C_3$ alkyl (e.g. 4-methyl pyridyl),
thienyl, and thienyl substituted with 1, 2, 3 or more substitutents selected from $C_1$-$C_3$ alkyl, $C_2$-$C_4$ alkenyl, and RO wherein R is selected from hydrogen and $C_1$-$C_3$ alkyl (e.g. 5-methyl thienyl);

n+m is 1 or 2, and $R^2$ is hydrogen; or
n is 1 or 2, and m is 1 or 0;
$R^2$ is selected from methyl, and hydroxyl;
$R^2$ forms together with the carbon atom to which it is attached a carbonyl group; or
$R^2$ is a bivalent atom, e.g. —CH—, —NH—, —O—, or —S—, forming together with one carbon atom of $R^1$ a 5 or 6 membered heterocyclic ring (e.g. $R^1$ and $R^2$ together with the carbon atoms to which they are attached is 2,3-dihydrobenzo[b][1,4]dioxin-2-yl);
$R^3$ is hydrogen, and $R^4$ and $R^5$ together with the carbon atom to which they are attached form p-menthyl; or
$R^3$ is methyl and $R^4$ and $R^5$ are iso-propyl.

The compounds according to the present invention comprise several chiral centres and as such exist as racemic or enantiomerically-enriched mixtures of enantiomers. Resolving stereoisomers or employing chiral starting material adds however to the cost of these cooling compounds, so it is preferred to use the compounds as racemic mixtures simply for economic reasons. However, if it is desired to prepare individual stereoisomers, this may be achieved according to methodology known in the art, e.g. preparative HPLC and GC on chiral stationary phases, by stereoselective synthesis, or starting from available chiral raw materials, such as optically active p-menthane carboxylic acid chloride, preferably (1R, 2S,5R)-2-isopropyl-5-methylcyclohexylic acid chloride.

As used in relation to compounds of formulae (I) unless otherwise indicated "substituted" refers to rings substituted with 1, 2, 3 or more substitutents selected from $C_1$-$C_3$ alkyl (e.g. methyl, ethyl), $C_2$-$C_4$ alkenyl (e.g. propenyl, isopropenyl, vinyl, isobutenyl), and RO wherein R is selected from hydrogen and $C_1$-$C_3$ alkyl (e.g. hydroxyl, methoxy, ethoxy, isopropoxy).

Non-limiting examples are compounds of formula (I) wherein $R^1$ is phenyl, phenyl substituted with one substituent selected from methyl, and methoxy, or pyridyl.

Further, non-limiting examples are compounds of formula (I) wherein $R^1$ is phenyl substituted in ortho- or meta-position with one substitutent selected from RO wherein R is selected from hydrogen, methyl ethyl and propyl.

Further, non-limiting examples are compounds of formula (I) wherein $R^1$ is phenyl substituted in ortho, meta- or para-position with one substituent selected from $C_1$-$C_3$ alkyl (e.g. methyl, ethyl), $C_2$-$C_4$ alkenyl (e.g. propenyl, isopropenyl, vinyl, isobutenyl).

Further, non-limiting examples are compounds of formula (I) wherein n+m is 2 and $R^2$ is hydrogen or hydroxyl.

Further, non-limiting examples are compounds of formula (I) wherein $R^3$ is hydrogen and $R^4$ and $R^5$ together with the carbon atom to which they are attached form p-menthyl (2-isopropyl-5-methylcyclohexyl), preferably (1R,2S,5R)-2-isopropyl-5-methylcyclohexyl.

In particular, embodiments are compounds of formula (I) selected from (1R,2S,5R)-2-isopropyl-5-methyl-N-(3-(o-tolyloxy)propyl)cyclohexane-carboxamide, (1R,2S,5R)-2-isopropyl-N-(3-(2-methoxyphenoxy)propyl)-5-methylcyclohexane-carboxamide, (1R,2S,5R)—N-(2-hydroxy-3-phenoxypropyl)-2-isopropyl-5-methylcyclohexane-carboxamide, (1R,2S,5R)-2-isopropyl-5-methyl-N-(2-phenoxypropyl)cyclohexanecarboxamide, (1R,2S,5R)—N-(2-(2,3-dihydrobenzo[b][1,4]dioxin-2-yl)ethyl)-2-isopropyl-5-methylcyclohexanecarboxamide, (1R,2S,5R)-2-isopropyl-5-methyl-N-(3-(pyridin-2-yloxy)propyl)cyclohexane-carboxamide, (1R,2S,5R)-2-isopropyl-5-methyl-N-(2-(p-tolyloxy)ethyl)-cyclohexanecarboxamide, (1R,2S,5R)-2-isopropyl-5-methyl-N-(2-phenoxyethyl)cyclohexanecarboxamide, 2-isopropyl-2,3-dimethyl-N-(2-phenoxypropyl)butanamide, 2-isopropyl-2,3-dimethyl-N-(3-(pyridin-2-yloxy)propyl)butanamide, 2-isopropyl-2,3-dimethyl-N-(2-phenoxyethyl)butanamide, 2-isopropyl-2,3-dimethyl-N-(3-phenoxypropyl)butanamide, and N-(2-hydroxy-3-phenoxypropyl)-2-isopropyl-2,3-dimethylbutanamide.

Amongst the compounds of the invention, (1R,2S,5R)-2-isopropyl-5-methyl-N-(2-phenoxyethyl)cyclohexanecarboxamide may be cited as a typical representative. When the cooling properties of this compound are compared with the prior art compound, (1R,2S,5R)-2-isopropyl-N-(2-methoxyethyl)-5-methylcyclohexane-carboxamide, the present compound possess a cooling intensity which is about 100 times higher.

The compounds of formula (I) may be used in products that are applied to mucous membranes such as oral mucosa, or to the skin, to give a cooling sensation. By "applying" is meant any form of bringing into contact, for example, oral ingestion, topical application or, in the case of tobacco products, inhalation. In the case of application to the skin, it may be, for example, by including the compound in a cream or salve, or in a sprayable composition. There is therefore also provided a method of providing a cooling sensation to the mucous membrane or skin by applying thereto a product comprising an effective amount of a compound as hereinabove described, or mixtures thereof.

Products that are applied to the oral mucosa may include foodstuffs and beverages taken into the mouth and swallowed, and products taken for reasons other than their nutritional value, e.g. tablets, troches, mouthwash, throat sprays, dentifrices and chewing gums, which may be applied to the oral mucosa for the purpose of cleaning, freshening, healing, and/or deodorising.

Products that are applied to the skin may be selected from perfumes, toiletries, cosmetic products such as lotions, oils, ointments and bathing agents, applicable to the skin of the human body, whether for medical or other reasons. Accordingly, in a further aspect there is provided a composition comprising an amount of at least one compound of formula (I) sufficient to stimulate the cold receptors in the areas of the skin or mucous membrane with which the composition comes into contact and thereby promote the desired cooling effect. A cooling effect may be achieved upon application of a product, for example, mouthwash or chewing gum, to the mucous membrane, e.g. oral mucosa, comprising less than 5000 ppm, in certain embodiments between 50 and 1000 ppm, such as about 200 ppm, of a compound of formula (I), or mixture thereof. If used for beverages the addition of about 5 ppm may be sufficient to achieve a cooling effect. For use in cosmetic products, the product may comprise from about 50 to about 5000 ppm. However, it is understood that the skilled person may employ compounds of formula (I), as hereinabove described, or a mixture thereof in amounts outside the aforementioned ranges to achieve sensorial effects.

Particular examples of foodstuffs and beverages may include, but are not limited to, beverages, alcoholic or non-alcoholic such as fruit juice beverages, fruit liquors, milk drinks, carbonated beverages, refreshing beverages, and health and nutrient drinks; frozen confectionery such as ice creams and sorbets; desserts such as jelly and pudding; confectionery such as cakes, cookies, chocolates, and chewing gum; jams; candies; breads; tea beverages such as green tea, black tea, chamomile tea, mulberry leaf tea, Roobos tea, peppermint tea; soaps; seasonings; instant beverages; snack foods and the like.

Further examples of products for topical application may include, but are not limited to, skin-care cosmetics such as cleansing tissues, talcum powders, face creams, lotions, tonics and gels; hand creams, hand- and body lotions, anticellulite/slimming creams and -lotions, lotions, balms, gels, sprays and creams; sunburn cosmetics including sunscreen lotions, balms, gels, sprays and creams; after sun lotions, sprays and creams; soaps, toothpicks, lip sticks, agents for bathing, deodorants and antiperspirants, face washing creams, massage creams, and the like, Further examples of products that are applied to the oral mucosa may include, but are not limited to, oral care products such as toothpastes, tooth gels, tooth powders, tooth whitening products, dental floss, anti-plaque and anti-gingivitis compositions, compositions for treatment of nasal symptoms, and gargle compositions.

Thus there is further provided an end-product selected from the group consisting of products that are applied to the oral mucosa and products that are applied to the skin, such as products for topical application, oral care products, nasal care products, toilet articles, ingestible products and chewing gum, and the like which comprises a product base and an effective amount of at least one cooling compound of formula (I) as defined herein above.

The compounds as hereinabove described may be used alone or in combination with other cooling compounds known in the art, e.g. menthol, menthone, isopulegol, N-ethyl p-menthanecarboxamide (WS-3), N,2,3-trimethyl-2-isopropylbutanamide (WS-23), ethyl 2-(2-isopropyl-5-methylcyclohexanecarboxamido)-acetate (WS-5), menthyl lactate, menthone glycerine acetal (Frescolat® MGA), mono-menthyl succinate (Physcool®), mono-menthyl glutarate, O-menthyl glycerine (CoolAct® 10) and 2-sec-butylcyclohexanone (Freskomenthe®), menthane, camphor, pulegol, cineol, mint oil, peppermint oil, spearmint oil, eucalyptus oil, 3-l-menthoxypropane-1,2-diol, 3-l-menthoxy-2-methylpropane-1,2-diol, p-menthane-3,8-diol, 2-l-menthoxyethane-1-ol, 3-l-menthoxypropane-1-ol, 4-l-menthoxybutane-1-ol, and menthyl pyrrolidone carboxylic acid compounds sold under the commercial name "Questice". Further examples of cooling compounds can be found e.g. in WO 2005/049553 (e.g. 2-isopropyl-5-methyl-cyclohexanecarboxylic acid (4-cyanomethyl-phenyl)-amide and 2-isopropyl-5-methyl-cyclohexanecarboxylic acid (4-cyano-phenyl)-amide), WO2006/125334 (e.g. 4-[(2-isopropyl-5-methyl-cyclohexanecarbonyl)-amino]-benzamide, 3-[(2-isopropyl-5-methyl-cyclohexanecarbonyl)-amino]benzamide, and (2-isopropyl-5-methyl-N-(4-(4-methylpiperazine-1-carbonyl)phenyl) cyclohexanecarboxamide) and WO 2007/019719 (e.g. 2-isopropyl-5-methyl-cyclohexanecarboxylic acid pyridin-2-ylamide, and 2-isopropyl-5-methyl-cyclohexanecarboxylic acid (2-pyridin-2-yl-ethyl)-amide), which are incorporated herein by reference.

Thus there is provided in a further aspect a composition for cooling comprising a compound of formula (I) as hereinabove defined, or a mixture thereof, optionally combined with at least one other cooling compound.

The cooling compounds of formula (I) may also be blended with known natural sensate compounds, for example, jambu, galangal, galangal acetate, sanshool, capscacian, pepper and ginger, or other flavour and fragrance ingredients generally known to the person skilled in the art. Suitable examples of flavour and fragrance ingredients include alcohols, aldehydes, ketones, esters, ethers, acetates, nitriles, terpene hydrocarbons, nitrogenous or sulphurous heterocyclic compounds. Flavor and fragrance ingredients may be of natural or synthetic origin. Many of these are listed in reference texts such as the book by S. Arctander, Perfume and Flavor Chemicals, 1969, Montclair, N.J., USA, or its more recent versions.

The cooling compounds may be employed into the products simply by directly mixing the compound with the product, or they may, in an earlier step, be entrapped with an entrapment material such as polymers, capsules, microcapsules and nanocapsules, liposomes, film formers, absorbents such as cyclic oligosaccharides, or they may be chemically bonded to a substrate, which are adapted to release the cooling compound upon application of an external stimulus such as temperature, moisture, and/or enzyme or the like, and then mixed with the product. Or they may be added white being solubilized, dispersed, or diluted using alcohols or polyhydric alcohols, such as, glycerine, propylene glycole, triazethine and mygliol, natural gums such as gum Arabic, or surfactants, such as glycerine fatty acid esters and saccharide fatty acid esters.

The compounds of formula (I) may be prepared by reacting the appropriate acid chloride of the formula $R^3R^4R^5C(O)Cl$ with an amine of the formula,

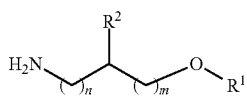

wherein $R^1$ to $R^5$, n and m have the same meaning as given above for the compounds of formula (I) in the presence of a base (e.g. pyridine triethyl amine, KOH, NaOH) under conditions known to the person skilled in the art. The amines and chlorides are commercially available and/or the person skilled in the art will know how to synthesize them from other commercially available starting materials.

The compositions and methods are now further described with reference to the following non-limiting examples.

These examples are for the purpose of illustration only and it is understood that variations and modifications can be made by one skilled in the art without departing from the scope of the invention. It should be understood that the embodiments described are not only in the alternative, but can be combined.

EXAMPLE 1

(1R,2S,5R)-2-isopropyl-5-methyl-N-(3-(o-tolyloxy)propyl)cyclohexane-carboxamide

In a 25 mL round bottom flask, fitted with magnetic stirrer, 10 mL of tetrahydrofurane, 6.0 mmol (1.5 eq.) of pyridine and 3.33 mmol of 2-phenoxyethanamine were added. p-Menthane carboxylic acid chloride (4.0 mmol) were added and the mixture was stirred at room temperature for 16 hours, over night. The reaction mixture was extracted with MTBE and HCl (1N in water). The organic layer was washed with NaOH (1N in water), dried over MgSO4 and concentrated. The crude product was purified by column chromatography or crystallized from MtBE and Hexane under dry ice cooling.

$^1$H NMR (300 MHz; CDCl$_3$) δ: 7.15 (d, 2H), 6.85 (m, 2H), 5.80 (s, 1H), 4.05 (t, 2H), 3.50 (dd, 2H), 2.25 (s, 3H), 2.05-1.90 (m, 3H), 1.80-1.60 (m, 4H), 1.60-1.45 (m, 1H), 1.4-1.15 (m, 2H), 1.05-0.90 (m, 2H), 0.87 (dd, 6H), 0.75 (d, 3H)

$^{13}$C NMR (75 MHz; CDCl$_3$) δ: 176, 131, 127, 127, 121, 111, 66, 50, 44, 40, 37, 35, 32, 29, 29, 24, 22, 21, 16, 16

GC/MS: 332 ([M+1]), 281, 224, 208, 180, 166, 152, 139, 124, 112, 99, 83, 69, 55, 41

Mp: 89.4-91.1° C.

EXAMPLE 2

Further Compounds

The following compounds were prepared following the general procedure as described in Example 1.

2.1: (1R,2S,5R)-2-isopropyl-N-(3-(2-methoxyphenoxy)propyl)-5-methylcyclohexane-carboxamide $^1$H NMR (300 MHz; CDCl$_3$) δ: 6.96-6.86 (m, 4H), 6.69 (s, 1H), 4.15-4.10 (m, 2H), 3.89 (s, 3H), 3.55-3.48 (m, 2H), 2.05-1.95 (m, 3H), 1.80-1.65 (m, 4H), 1.65-1.50 (m, 1H), 1.4-1.15 (m, 2H), 1.10-0.95 (m, 2H), 0.87 (d, 6H), 0.75 (d, 3H)

GC/MS: 316 ([M+1]), 281, 224, 208, 180, 166, 149, 139, 123, 112, 95, 83, 69, 55, 41

Mp: 107.3-109.9° C.

2.2: (1R,2S,5R)—N-(2-hydroxy-3-phenoxypropyl)-2-isopropyl-5-methylcyclohexane-carboxamide $^1$H NMR (300 MHz; CDCl$_3$) δ: 7.27 (t, 2H), 6.95 (t, 1H), 6.90 (d, 2H), 6.10 (s, 1H), 4.15 (m, 1H), 3.95 (d, 2H), 4.0-3.8 (b, 1H), 3.70-3.55 (m, 1H), 3.50-3.35 (m, 1H), 2.10-2.00 (m, 1H), 1.80-1.60 (m, 4H), 1.60-1.45 (m, 1H), 1.45-1.15 (m, 3H), 1.05-0.95 (m, 2H), 0.87 (m, 6H), 0.75 (dd, 3H)

$^{13}$C NMR (75 MHz; CDCl$_3$) δ: 178, 158, 130, 121, 114, 70, 69, 49, 44, 44, 43, 39, 35, 32, 29, 27, 24, 22, 21, 16

GC/MS: 333 ([M+1]), 315, 290, 272, 258, 240, 222, 204, 191, 167, 139, 123, 107, 94, 83, 69, 55, 41

2.3: (1R,2S,5R)-2-isopropyl-5-methyl-N-(2-phenoxypropyl)cyclohexanecarboxamide $^1$H NMR (300 MHz; CDCl$_3$) δ: 7.30-7.24 (m, 2H), 6.97-6.87 (m, 3H), 5.95 (s, 1H), 4.54-4.48 (m, 1H), 3.75-3.60 (m, 1H), 3.40-3.20 (m, 1H), 2.05-1.95 (m, 1H), 1.80-1.40 (m, 5H), 1.45-1.15 (m, 5H), 1.10-0.60 (m, 11H)

LC/MS: 340 (M+Na), 318 ([M+1])

2.4: (1R,2S,5R)—N-(2-(2,3-dihydrobenzo[b][1,4]dioxin-2-yl)ethyl)-2-isopropyl-5-methylcyclohexanecarboxamide $^1$H NMR (300 MHz; CDCl$_3$) δ: 7.94 (d, 1H), 6.87-6.78 (m, 1H), 4.27-4.25 (m, 1H), 4.15-4.13 (m, 1H), 3.91-3.84 (dd, 1H), 3.33-3.21 (m, 2H), 2.05 (t, 1H), 1.80-1.50 (m, 6H), 1.40-1.20 (m, 2H), 1.10-0.80 (m, 9H), 0.75 (t, 3H)

LC/MS: 368 (M+Na)

2.5: (1R,2S,5R)-2-isopropyl-5-methyl-N-(3-(pyridin-2-yloxy)propyl)cyclohexane-carboxamide $^1$H NMR (300 MHz; CDCl$_3$) δ: 8.25 (d, 1H), 8.19 (d, 1H), 7.20-7.16 (m, 2H), 6.77 (t, 1H), 4.06-4.02 (t, 2H), 3.60-3.45 (m, 2H), 2.10-2.00 (m, 1H), 1.80-1.65 (m, 4H), 1.60-1.50 (t, 1H), 1.40-1.20 (m, 2H), 1.10-0.80 (m, 8H), 0.77 (d, 3H)

LC/MS: 341 (M+Na), 319 (M+1)

2.6: (1R,2S,5R)-2-isopropyl-5-methyl-N-(2-(p-tolyloxy)ethyl)cyclohexanecarboxamide $^1$H NMR (300 MHz; CDCl$_3$) δ: 7.10 (d, 2H), 6.80 (d, 2H), 5.80 (s, 1H), 4.02 (t, 2H), 3.67-3.63 (m, 2H), 2.29 (s, 3H), 2.01 (t, 1H), 1.80-1.50 (m, 5H), 1.40-1.20 (m, 2H), 1.10-0.90 (m, 2H), 0.87 (t, 6H), 0.75 (d, 3H)

LC/MS: 340 (M+Na), 318 (M+1)

2.7: (1R,2S,5R)-2-isopropyl-5-methyl-N-(2-phenoxyethyl)cyclohexanecarboxamide $^1$H NMR (300 MHz; CDCl$_3$) δ: 7.30 (t, 1H), 6.97 (t, 1H), 6.90 (d, 2H), 5.87 (s, 1H), 4.04 (t, 2H), 3.70-3.63 (m, 2H), 2.01 (t, 1H), 1.80-1.65 (m, 4H), 1.60-1.50 (m, 1H), 1.40-1.20 (m, 2H), 1.10-0.90 (m, 2H), 0.87 (1, 6H), 0.75 (d, 3H)

LC/MS: 326 (M+Na), 304 (M+1)

EXAMPLE 3

Further Compounds

The following compounds can be prepared following the general procedure as described in Example 1, starting from 2-isopropyl-2,3-dimethylbutanoyl chloride and the appropriated amine.

3.1: 2-Isopropyl-2,3-dimethyl-N-(2-phenoxypropyl)butanamide 3.2: 2-Isopropyl-2,3-dimethyl-N-(3-(pyridin-2-yloxy)propyl)butanamide 3.3: 2-Isopropyl-2,3-dimethyl-N-(2-phenoxyethyl)butanamide 3.4: 2-Isopropyl-2,3-dimethyl-N-(3-phenoxypropyl)butanamide 3.5: N-(2-Hydroxy-3-phenoxypropyl)-2-isopropyl-2,3-dimethylbutanamide

EXAMPLE 4

Cooling Intensity

A small group of panelists was asked to taste various aqueous solutions of compounds of formula (I) and indicate which solutions had a cooling intensity similar to or slightly higher than that of a solution of menthol at 2 ppm. The results are shown in Table 1.

TABLE 1

| Chemical | Concentration | Odor |
|---|---|---|
| Comparison: I-Menthol | 2.0 ppm | Minty |
| Comparison: N-ethyl p-menthanecarboxamide (WS-3) | 1.5 ppm | None |
| Comparison: (1R,2S,5R)-2-isopropyl-N-(2-methoxyethyl)-5-methylcyclohexanecarboxamide | 1.0 ppm | None |
| Comparison: (1R,2S,5R)-N-(3-isopropoxypropyl)-2-isopropyl-5-methylcyclohexanecarboxamide | 0.1 ppm | None |
| (1R,2S,5R)-2-isopropyl-5-methyl-N-(2-phenoxyethyl)cyclohexanecarboxamide (Ex. 2.7) | 0.01 ppm | None |
| (1R,2S,5R)-2-isopropyl-5-methyl-N-(3-(pyridin-2-yloxy)propyl)cyclohexanecarboxamide (Ex. 2.5) | 0.02 ppm | None |

EXAMPLE 5

Application in Toothpaste 0.10 g of (1R,2S,5R)—N-(2-hydroxy-3-phenoxypropyl)-2-isopropyl-5-methylcyclohexane-carboxamide (at 10% by weight solved in ethanol) and 0.30 g saccharin were mixed in a toothgel base.

A piece of the thus prepared toothpaste was put on a toothbrush and a panelist's teeth were brushed. The mouth was rinsed with water and the water spat out. A long lasting cooling sensation was felt by the panelist in all areas of the mouth. The cooling sensation was perceived for over 50 minutes.

The invention claimed is:

1. A compound of formula (I)

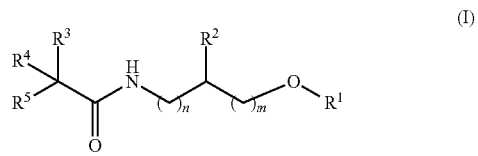

wherein

R$^1$ is selected from phenyl, phenyl substituted with 1, 2, 3 or more substitutents selected from C$_1$-C$_3$ alkyl, C$_2$-C$_4$ alkenyl, and RO wherein R is selected from hydrogen and C$_1$-C$_3$ alkyl, pyridyl, pyridyl substituted with 1, 2, 3 or more substitutents selected from C$_1$-C$_3$ alkyl, C$_2$-C$_4$ alkenyl, and RO wherein R is selected from hydrogen and C$_1$-C$_3$ alkyl, thienyl, and thienyl substituted with 1, 2, or 3 substitutents selected from C$_1$-C$_3$ alkyl, C$_2$-C$_4$ alkenyl, and RO wherein R is selected from hydrogen and C$_1$-C$_3$ alkyl;

n+m is 1 or 2, and R$^2$ is hydrogen; or n is 1 or 2, and m is 1 or 0;

R$^2$ is selected from methyl, and hydroxyl;

or

R$^2$ is a bivalent atom forming together with one carbon atom of R$^1$ a 5 or 6 membered heterocyclic ring;

R$^3$ is hydrogen, and R$^4$ and R$^5$ together with the carbon atom to which they are attached form p-menthyl; or R$^3$ is methyl and R$^4$ and R$^5$ are iso-propyl.

2. A compound selected from the group consisting of (1R,2S,5R)-2-isopropyl-5-methyl-N-(3-(o-tolyloxy)propyl)cyclohexane-carboxamide, (1R,2S,5R)-2-isopropyl-N-(3-(2-methoxyphenoxy)propyl)-5-methyl cyclohexane-carboxamide, (1R,2S,5R)—N-(2-hydroxy-3-phenoxypropyl)-2-isopropyl-5-methylcyclohexane-carboxamide, (1R,2S,5R)-2-isopropyl-5-methyl-N-(2-phenoxy propyl)cyclohexane-carboxamide, (1R,2S,5R)—N-(2-(2,3-dihydrobenzo[b][1,4]dioxin-2-yl)ethyl)-2-isopropyl-5-methylcyclohexane carboxamide, (1R,2S,5R)-2-isopropyl-5-methyl-N-(3-(pyridin-2-yloxy)propyl) cyclohexane-carboxamide, (1R,2S,5R)-2-isopropyl-5-methyl-N-(2-(p-tolyloxy)ethyl)cyclohexanecarboxamide, (1R,2S,5R)-2-isopropyl-5-methyl-N-(2-phenoxyethyl)cyclohexanecarboxamide, 2-isopropyl-2,3-dimethyl-N-(2-phenoxypropyl)-butanamide, 2-isopropyl-2,3-dimethyl-N-(3-(pyridin-2-yloxy)-propyl)butanamide, 2-isopropyl-2,3-dimethyl-N-(2-phenoxyethyl)butanamide, 2-isopropyl-2,3-dimethyl-N-(3-phenoxypropyl)butanamide, and N-(2-hydroxy-3-phenoxypropyl)-2-isopropyl-2,3-dimethylbutanamide.

3. A composition for cooling comprising at least one compound of formula (I) as defined in claim 1.

4. A composition for cooling according to claim 3 further comprising at least one other cooling compound.

5. A composition according to claim 4 wherein the at least one other cooling compound is selected from the group consisting of menthol, menthone, isoputegol, N-ethyl p-menthanecarboxamide, N,2,3-trimethyl-2-isopropylbutanamide, ethyl-[[5-methyl-2-(isopropyl)cyclohexyl]carbonyl]glycinate, menthyl lactate, menthone glycerine acetal, mono-menthyl succinate, mono-menthyl glutarate, O-menthyl glycerine, 2-sec-butylcyclohexanone, menthane, camphor, pulegol, cineol, mint oil, peppermint oil, spearmint oil, eucalyptus oil, 3-l-menthoxypropane-1,2-diol, 3-l-menthoxy-2-methylpropane-1,2-diol, p-menthane-3,8-diol, 2-l-menthoxyethane-1-ol, 3-1-menthoxypropane-1-ol, 4-l-menthoxybutane-1-ol, 2-isopropyl-5-methyl-cyclohexanecarboxylic acid (4-cyanomethyl-phenyl)-amide, 2-isopropyl-5-methyl-cyclohexanecarboxylic acid (4-cyano-phenyl)-amide, 4-[(2-isopropyl-5-methyl-cyclohexanecarbonyl)-amino]-benzamide, 3-[(2-isopropyl-5-methyl-cyclohexanecarbonyl)-amino]benzamide, (2-isopropyl-5-methyl-N-(4-(4-methylpiperazine-1-carbonyl)phenyl)cyclohexanecarboxamide, 2-isopropyl-5-methyl-cyclohexanecarboxylic acid pyridin-2-ylamide, 2-isopropyl-5-methyl-cyclohexanecarboxylic acid (2-pyridin-2-yl-ethyl)-amide, and mixtures thereof.

6. A product selected from the group consisting of products that are applied to the oral mucosa and products that are applied to the skin, said product comprising a product base and an effective amount of at least one compound of formula (I) as defined in claim 1.

7. A product according to claim 6 further comprising at least one other cooling compound.

8. A product according to claim 7 wherein the at least one other cooling compound is selected from the group consisting of menthol, menthone, isoputegol, N-ethyl p-menthanecarboxamide, N,2,3-trimethyl-2-isopropylbutanamide, ethyl-[[5-methyl-2-(isopropyl)cyclohexyl]carbonyl]glycinate, menthyl lactate, menthone glycerine acetal, mono-menthyl succinate, mono-menthyl glutarate, O-menthyl glycerine, 2-sec-butylcyclohexanone, menthane, camphor, pulegol, cineol, mint oil, peppermint oil, spearmint oil, eucalyptus oil, 3-l-menthoxypropane-1,2-diol, 3-l-menthoxy-2-methylpropane-1,2-diol, p-menthane-3,8-diol, 2-l-menthoxyethane-1-ol, 3-1-menthoxypropane-1-ol, 4-l-menthoxybutane-1-ol, 2-isopropyl-5-methyl-cyclohexanecarboxylic acid (4-cyanomethyl-phenyl)-amide, 2-isopropyl-5-methyl-cyclohexanecarboxylic acid (4-cyano-phenyl)-amide, 4-[(2-isopropyl-5-methyl-cyclohexanecarbonyl)-amino]-benzamide, 3-[(2-isopropyl-5-methyl-cyclohexanecarbonyl)-amino]benzamide, (2-isopropyl-5-methyl-N-(4-(4-methylpiperazine-1-carbonyl)phenyl)cyclohexanecarboxamide, 2-isopropyl-5-methyl-cyclohexanecarboxylic acid pyridin-2-ylamide, 2-isopropyl-5-methyl-cyclohexanecarboxylic acid (2-pyridin-2-yl-ethyl)-amide, and mixtures thereof.

9. A product selected from the group consisting of products that are applied to the oral mucosa and products that are applied to the skin, said product comprising a product base and an effective amount of at least one compound selected from the group consisting of (1R,2S,5R)-2-isopropyl-5-methyl-N-(3-(o-tolyloxy)propyl)cyclohexane-carboxamide, (1R,2S,5R)-2-isopropyl-N-(3-(2-methoxyphenoxy)propyl)-5-methylcyclohexane-carboxamide, (1R,2S,5R)—N-(2-hydroxy-3-phenoxypropyl)-2-isopropyl-5-methylcyclohexane-carboxamide, (1R,2S,5R)-2-isopropyl-5-methyl-N-(2-phenoxypropyl)cyclohexane-carboxamide, (1R,2S,5R)—N-(2-(2,3-dihydrobenzo[b][1,4]dioxin-2-yl)ethyl)-2-isopropyl-5-methylcyclohexanecarboxamide, (1R,2S,5R)-2-isopropyl-5-methyl-N-(3-(pyridin-2-yloxy)-propyl)cyclohexane-carboxamide, (1R,2S,5R)-2-isopropyl-5-methyl-N-(2-(p-tolyloxy)ethyl)cyclohexanecarboxamide, (1R,2S,5R)-2-isopropyl-5-methyl-N-(2-phenoxyethyl)cyclohexanecarboxamide, 2-isopropyl-2,3-dimethyl-N-(2-phenoxy propyl)-butanamide, 2-isopropyl-2,3-dimethyl-N-(3-(pyridin-2-yloxy)-propyl)butanamide, 2-isopropyl-2,3-dimethyl-N-(2-phenoxyethyl)butanamide, 2-isopropyl-2,3-dimethyl-N-(3-phenoxypropyl)butanamide, N-(2-hydroxy-3-phenoxypropyl)-2-isopropyl-2,3-dimethylbutanamide and mixtures thereof.

10. A product according to claim 9 further comprising at least one other cooling compound.

11. The product according to claim 10 wherein the at least one other cooling compound is selected from the group consisting of menthol, menthone, isoputegol, N-ethyl p-menthanecarboxamide, N,2,3-trimethyl-2-isopropylbutanamide, ethyl-[[5-methyl-2-(isopropyl)cyclohexyl]carbonyl]glycinate, menthyl lactate, menthone glycerine acetal, mono-menthyl succinate, mono-menthyl glutarate, O-menthyl glycerine, 2-sec-butylcyclohexanone, menthane, camphor, pulegol, cineol, mint oil, peppermint oil, spearmint oil, eucalyptus oil, 3-l-menthoxypropane-1,2-diol, 3-l-menthoxy-2-methylpropane-1,2-diol, p-menthane-3,8-diol, 2-l-menthoxyethane-1-ol, 3-1-menthoxypropane-1-ol, 4-l-menthoxybutane-1-ol, 2-isopropyl-5-methyl-cyclohexanecarboxylic acid (4-cyanomethyl-phenyl)-amide, 2-isopropyl-5-methyl-cyclohexanecarboxylic acid (4-cyano-phenyl)-amide, 4-[(2-isopropyl-5-methyl-cyclohexanecarbonyl)-amino]-benzamide, 3-[(2-isopropyl-5-methyl-cyclohexanecarbonyl)-amino]benzamide, (2-isopropyl-5-methyl-N-(4-(4-methylpiperazine-1-carbonyl)phenyl)cyclohexanecarboxamide, 2-isopropyl-5-methyl-cyclohexanecarboxylic acid pyridin-2-ylamide, 2-isopropyl-5-methyl-cyclohexanecarboxylic acid (2-pyridin-2-yl-ethyl)-amide, and mixtures thereof.

12. A composition for cooling comprising at least one compound as defined in claim 2.

13. The composition for cooling according to claim 12 further comprising at least one other cooling compound.

14. The composition according to claim 13 wherein the at least one other cooling compound is selected from the group consisting of menthol, menthone, isoputegol, N-ethyl p-menthanecarboxamide, N,2,3-trimethyl-2-isopropylbutanamide, ethyl-[[5-methyl-2-(isopropyl)cyclohexyl]carbonyl]glycinate, menthyl lactate, menthone glycerine acetal, mono-menthyl succinate, mono-menthyl glutarate, O-menthyl glycerine, 2-sec-butylcyclohexanone, menthane, camphor, pulegol, cineol, mint oil, peppermint oil, spearmint oil, eucalyptus oil, 3-l-menthoxypropane-1,2-diol, 3-1-menthoxy-2-methylpropane-1,2-diol, p-menthane-3,8-diol, 2-l-menthoxyethane-1-ol, 3-1-menthoxypropane-1-ol, 4-l-menthoxybutane-1-ol, 2-isopropyl-5-methyl-cyclohexanecarboxylic acid (4-cyanomethyl-phenyl)-amide, 2-isopropyl-5-methyl-cyclohexanecarboxylic acid (4-cyano-phenyl)-amide, 4-[(2-isopropyl-5-methyl-cyclohexanecarbonyl)-amino]-benzamide, 3-[(2-isopropyl-5-methyl-cyclohexanecarbonyl)-amino]benzamide, (2-isopropyl-5-methyl-N-(4-(4-methylpiperazine-1-carbonyl)phenyl)cyclohexanecarboxamide, 2-isopropyl-5-methyl-cyclohexanecarboxylic acid pyridin-2-ylamide, 2-isopropyl-5-methyl-cyclohexanecarboxylic acid (2-pyridin-2-yl-ethyl)-amide, and mixtures thereof.

15. A method of providing a cooling sensation to the skin or mucosa membrane by applying thereto a compound of formula (I) as defined in claim 1.

16. A method of providing a cooling sensation to the skin or mucosa membrane by applying thereto a compound as defined in claim 2.

* * * * *